(12) United States Patent
Mangia et al.

(10) Patent No.: US 6,395,901 B1
(45) Date of Patent: May 28, 2002

(54) PROCESS FOR THE PREPARATION OF ALKYL MERCAPTO METHYL ERGOLINE DERIVATIVES

(75) Inventors: Alberto Mangia, Basiglio; Paride Grisenti, Milan, both of (IT)

(73) Assignee: Poli Industria Chimica S.p A., Milan (IT)

( * ) Notice: Subject to any disclaimer, the term of this patent is extended or adjusted under 35 U.S.C. 154(b) by 0 days.

(21) Appl. No.: 09/787,934

(22) PCT Filed: Dec. 31, 2000

(86) PCT No.: PCT/EP99/10493

§ 371 (c)(1),
(2), (4) Date: Mar. 21, 2001

(87) PCT Pub. No.: WO00/44748

PCT Pub. Date: Aug. 3, 2000

(30) Foreign Application Priority Data

Jan. 27, 1999 (IT) .......................................... MI99A0146

(51) Int. Cl.$^7$ ..................... C07D 457/02; C07D 457/04
(52) U.S. Cl. ........................................... 546/67; 546/89
(58) Field of Search ..................................... 546/67, 69

(56) References Cited

U.S. PATENT DOCUMENTS

| 4,166,182 A | 8/1979 | Kornfeld et al. ............... 546/67 |
| 4,246,265 A | 1/1981 | Kornfeld et al. ............. 424/261 |

FOREIGN PATENT DOCUMENTS

| EP | 0 003 667 A1 | 8/1979 | ......... C07D/457/02 |
| EP | 0 213 850 A2 | 3/1987 | ......... C07D/457/02 |
| EP | 0 571 202 A1 | 11/1993 | ......... C07D/457/02 |

OTHER PUBLICATIONS

Misner, Jerry W., et al., "Pergolide: Process design challenges of a potent drug," *Chemtech*:28–33 (Nov. 1996).

Misner, Jerry W., et al., "Integration of a Highly Selective Demethylation of a Quaternized Ergoline into a One–Pot Synthesis of Pergolide," *Organic Process Research & Development* 1: 77–80 (1997).

Primary Examiner—Charanjit S. Aulakh
(74) Attorney, Agent, or Firm—Darby & Darby

(57) ABSTRACT

Process for the preparation of compounds active in the treatment of Parkinson's disease, and such compounds, having general formula (VI) wherein $R_4$ may be, independently, a linear, branched or cyclic, saturated or unsaturated $C_{1-8}$ alkyl radical, such as, for example, the radicals methyl, ethyl, propyl, butyl, isobutyl, tert-butyl, pentyl, cyclopentyl, hexyl, cyclohexyl and octyl. The process utilizes as starting materials the compound of formula (I) wherein $R_1$ represents a linear, branched or cyclic, saturated or unsaturated $C_{1-8}$ alkyl residue.

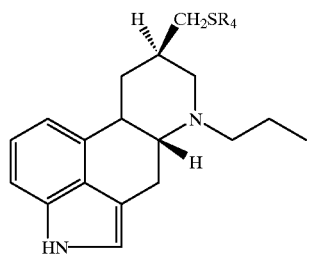

(VI)

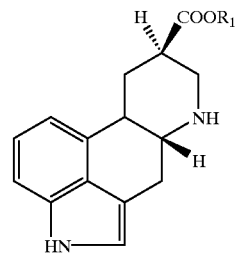

(I)

29 Claims, No Drawings

PROCESS FOR THE PREPARATION OF ALKYL MERCAPTO METHYL ERGOLINE DERIVATIVES

The present invention relates to the preparation of pharmaceutical active ingredients, and in particular to the preparation of medicaments active in the treatment of Parkinson's disease.

PRIOR ART

Alkaloids having an ergoline structure exhibit a wide spectrum of biological effects which include both peripheral effects (vasoconstrictor and contractile effect on the smooth muscle of the uterus) and effects on the central nervous system (various sites of action are located in vasomotor centres and cardiac inhibitor centres found in the medulla oblongata and in sympathetic structures found in the diencephalon).

Some of those alkaloids, such as ergotamnine, ergometrinc, ergosine, crgocrystine and ergocryptine, are entirely of natural origin because they can be isolated from the fungus *Claviceps purpurea*. That fungus is a member of the class of Ascomycetes which is capable of infesting many cereals, such as rye, barley and wheat; its sclerotium contains a high percentage (0.5–0.8% by weight) of alkaloids having an ergoline structure which are responsible for its known toxic properties. Other compounds are of a semi-synthetic nature and are prepared by chemical modification of naturally occurring alkaloids having an ergoline structure. Noteworthy among the above-mentioned semi-synthetic derivatives are bromocryptine, [CAS 25614-03-3], lysuride [CAS 18016-80-3) and pergolide (FIG. 1), namely (8)-8-[(methylthio)methyl]-6-propylergoline [CAS 66104-22-1]; this last-mentioned compound in particular is a semi-synthetic ergoline used in therapy for the treatment of Parkinson's disease

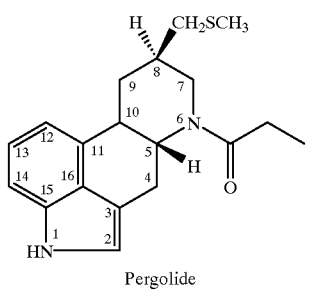

Pergolide

Fig. 1

The processes for the synthesis and purification of that molecule are described in U.S. Pat. No. 4,166,182 and U.S. Pat. No. 5,463,060; those patents, however, describe synthetic approaches which, according to the authors themselves, are not entirely satisfactory from several points of view. The impurities which arise during the synthesis processes described in U.S. Pat. No. 4,166,182 and U.S. Pat. No. 5,463,060 are difficult to remove without significant losses in yield (J. Kennedy et al., Org. Process Res. Dev. (1997), 1(1), 68–71); furthermore, the process described in U.S. Pat. No. 4,166,182, has low yields and requires long operating times (J. W. Misner et al., Book of Abstracts, 210th ACS National Meeting, Chicago, Ill., Aug. 20–24 (995). Publisher: American Chemical Society, Washington, D.C.).

To be more precise, U.S. Pat. No. 4,166,182 describes the synthesis of pergolide mesylate with 22% yields starting from D-8-methoxycarbonylergoline. The synthesis and chromatographic purification steps make the process particularly complicated; the basic pergolide, obtained with a 38% yield starting from D-8-methoxycarbonylergoline, also requires a further purification step by salification using methanesulphonic acid.

U.S. Pat. No. 5,463,060, on the other hand, describes the synthesis of the basic pergolide starting from 8,9-dihydroelymoclavine with 90.8% yields and with a titre of 94.1%. 8,9-dihydroelymoclavine (CAS 18051-16-6) is, however, a semi-synthetic alkaloid derivative which is not readily available because it is obtained from lysergic acid by means of numerous synthesis steps (see, for example: HU 89-3223 890627; R. Voigt et al. *Phanirazie* (1973), 2; S. Miroslav et al. Collect.Czech.Chem.Commun. (1968), 33(2), 577–82); the synthetic steps necessary to carry out the above-mentioned conversion arc also especially onerous because they require, inter alia, stereoselective hydrogenation of the double bond in the 9,10 position and the reduction of the 8 carboxylic function to an alcoholic function (upon conversion into methyl ester).

The object of the present invention is therefore to provide an alternative process for the production of pergolide which permits yields and purities higher than those of U.S. Pat. No. 4,166,182 and which uses a starting compound which is more readily available than 8,9-dihydroelymoclavine.

SUBJECT-MATTER OF THE INVENTION

Medicaments active in the treatment of Parkinson's disease which can be prepared in accordance with the process of the present invention comprise products which have the following general formula VI:

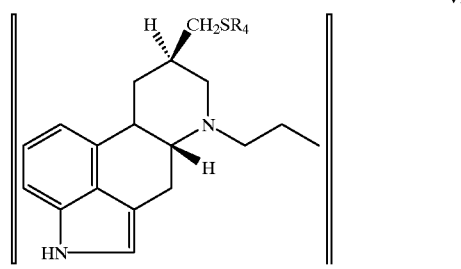

VI wherein $R_4$ may be, independently, a linear, branched or cyclic, saturated or unsaturated $C_{1-8}$ alkyl radical, such as, for example, the radicals methyl, ethyl, propyl, butyl, isobutyl, tert-butyl, pentyl, cyclopentyl, hexyl, cyclohexyl and octyl; the preferred compound includes, but is not limited only to, the pergolide ($R_4$=$CH_3$).

The process for the synthesis of those compounds, which forms the main subject of the present invention, uses as starting material the compound of formula I given below, wherein $R_1$ represents a linear, branched or cyclic, saturated or unsaturated $C_{1-8}$ akyl residue, preferably methyl, ethyl, propyl, butyl, isobutyl, tert-butyl, pentyl, cyclopentyl, hexyl, cyclohexyl and octyl, and even more preferably methyl, or the well known and readily available D-8-methoxycarbonylergoline [CAS 30341-92-5].

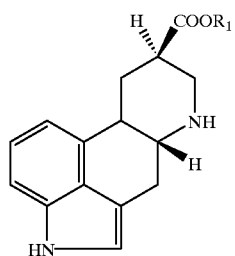

In that process, the compounds of formula I are reacted with 3-halo- and/or 2-halo-propionyl chloride in an aprotic organic solvent in the presence of a suitable proton acceptor. Solvents that may be used in that step are preferably selected from acetone, methyl ethyl ketone, tetrahydrofuran and dimethylformamide; the proton acceptor is preferably selected from triethylaniine, pyridine and lutidine. Both the proton acceptor and the 3-halo- and/or 2-halo-propionyl chloride are preferably used in equimolar amounts relative to the compound of formula I.

The compound or mixture of compounds IIa and IIb so obtained is then reacted with calcium borohydride in an amount of preferably from 5 to 9 moles/mole of substrate in tetrahydrofuran. The tetrahydrofuran is preferably present in an amount of from 2 to 8 ml per gram of substrate; optionally, it may be used in admixture with protic organic solvents, such as methanol, ethanol or isopropanol, or with an aqueous-alcoholic solution thereof. The reaction is carried out at a temperature of from 10 to 65° C., preferably at 60° C.

Compound III so obtained is then reacted in an aprotic organic solvent with an alkylsulphonyl chloride in the presence of a proton acceptor at a temperature of preferably from 10 to 30° C.; the proton acceptors are preferably selected from pyridine, triethylaniine, lutidine; the alkylsulphonyl chlorides are preferably selected from methanesulphonyl chloride, ethanesulphonyl chloride and p-toluenesulphonyl chloride. The proton acceptor and the alkylsulphonyl chloride are preferably used in amounts of from 20 to 30 and from 1.2 to 3 moles/mole of substrate, respectively.

Compound IV so obtained is then reacted in an aprotic organic solvent with a compound of the general formula $R_4SX$, wherein $R_4$ is a linear, branched or cyclic, saturated or unsaturated $C_{1-8}$ alkyl residue, preferably methyl, and X is an alkali metal, preferably sodium. The compound $R_4SX$ is preferably used in an amount equal to 4–8 equivalents relative to the substrate; the apolar organic solvent is preferably dimethylformamide; the reaction is preferably carried out at a temperature of from 90 to 100° C.

Finally, compound V so obtained is converted into the desired end product by treatment with a reducing agent in an aprotic organic solvent at a temperature of preferably from 20 to 45° C. Reducing agents that may be used in that step are preferably selected from lithium aluminium hydride and sodium dihydro-bis(2-methoxyethoxy)aluminate; aprotic solvents that may be used in that step are preferably selected from tetrahydrofuran, dioxane and toluene.

For greater clarity, the novel process according to the present invention is shown in the following reaction schemes 1, 2 and 3.

Scheme 1

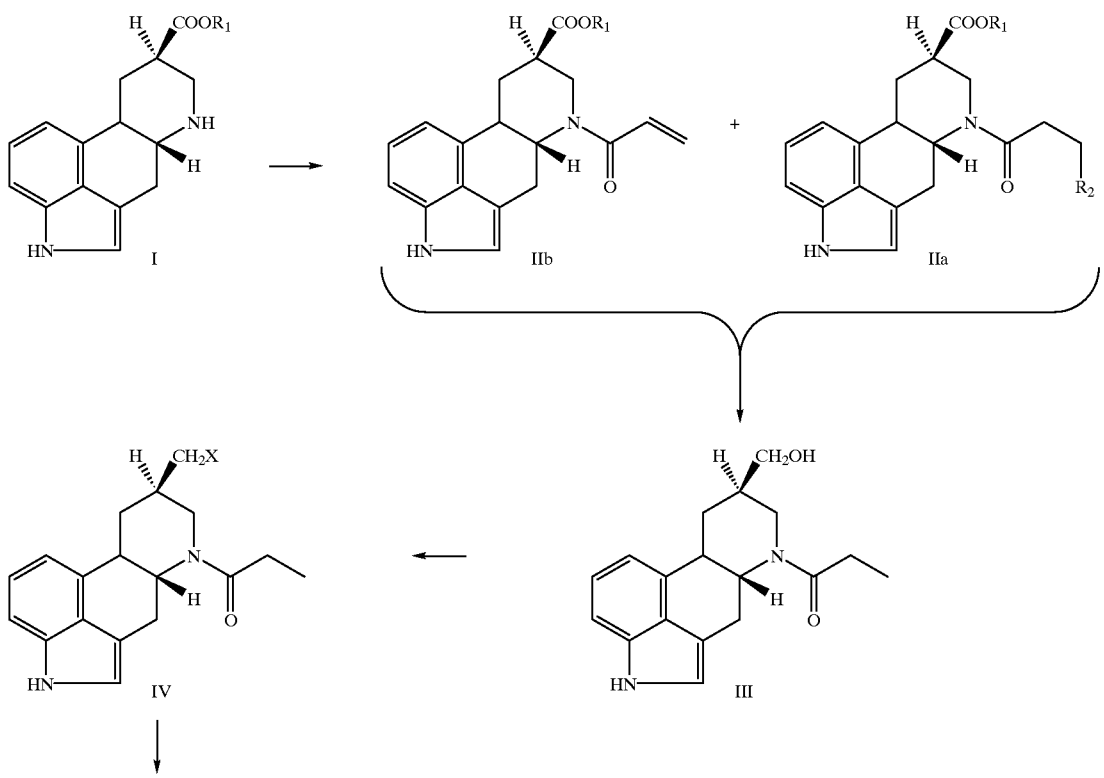

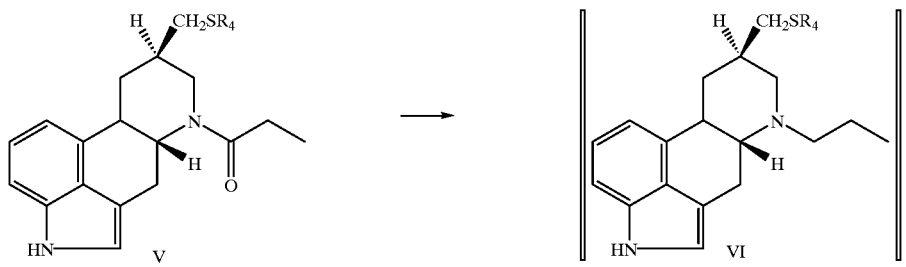

wherein $R_1$ represents a linear, branched or cyclic, saturated or unsaturated $C_{1-8}$ alkyl residue, such as, for example, the radicals methyl, ethyl, propyl, butyl, isobutyl, tert-butyl, pentyl, cyclopentyl, hexyl, cyclohexyl and octyl, preferably a methyl group; $R_2$ is a halogen (Cl, I, Br), preferably chlorine (Cl), X is an iodine molecule or a compound of the general formula $R_5SO_3$ wherein $R_5$ is methyl, ethyl or p-tolyl, preferably methyl; $R_4$ is, independently, a linear, branched or cyclic, saturated or unsaturated $C_{1-8}$ alkyl residue, such as, for example, the radicals methyl, ethyl, propyl, butyl, isobutyl, tert-butyl, pentyl, cyclopentyl, hexyl, cyclohexyl, preferably a methyl group.

Scheme 2

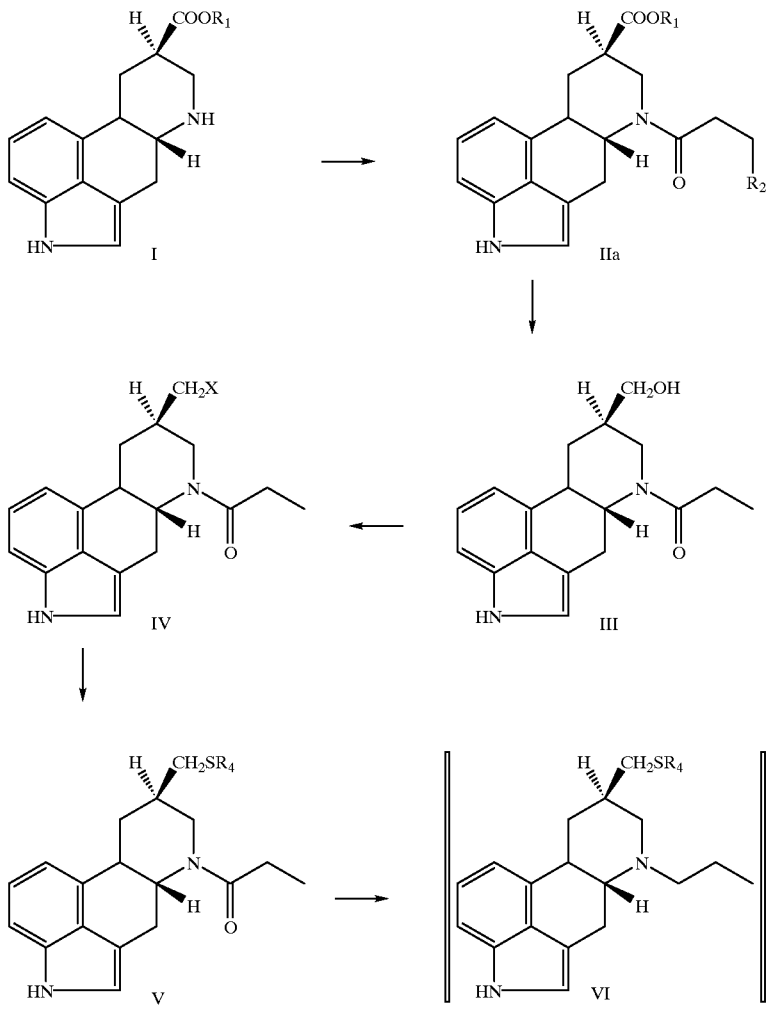

wherein $R_1$, $R_2$, $R_4$ and X have been defined above.

Scheme 3

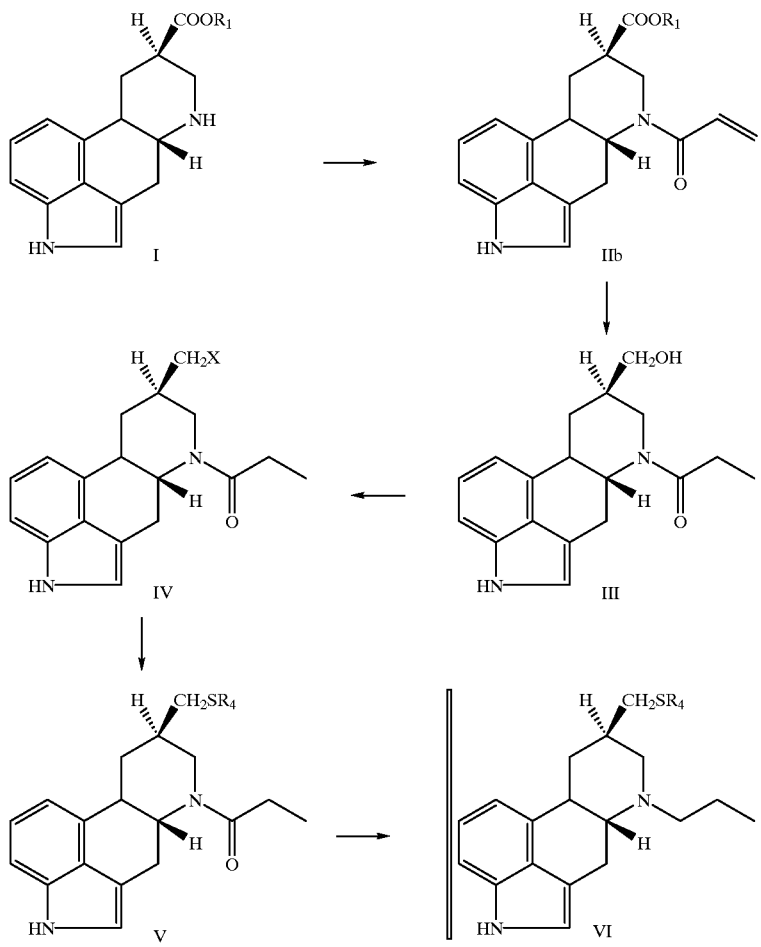

wherein $R_1$, $R_4$ and X have been defined above.

The novel intermediates of formula II, III, IV and V, which are given individually below for greater clarity, constitute a further subject of the invention.

II

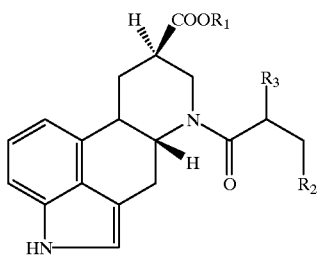

wherein $R_1$ and $R_3$ may be a halogen (Cl, I, Br) and hydrogen (H), respectively; alternatively, $R_2$ and $R_3$ may be bonded to one another directly giving rise to a double bond; and $R_1$ represents a linear, branched or cyclic, saturated or unsaturated $C_{1-8}$ alkyl residue, such as, for example, the radicals methyl, ethyl, propyl, butyl, isobutyl, tert-butyl, pentyl, cyclopentyl, hexyl, cyclohexyl and octyl; the preferred molecules are represented by the compounds IIa ($R_3$=H; $R_2$=Cl; $R_1$=$CH_3$) and IIb ($R_3$ and $R_2$ joined together to give rise to a double bond; $R_1$=$CH_3$).

III

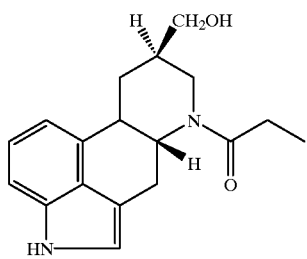

IV

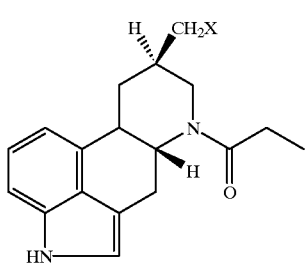

wherein X is a halogen (X=I, compound IVb) or a compound of the general formula $R_5SO_3$— wherein $R_1$ ismethyl, ethyl or p-tolyl; the preferred molecule is represented by the compound IVa(X=CH$_3$SO$_3$—).

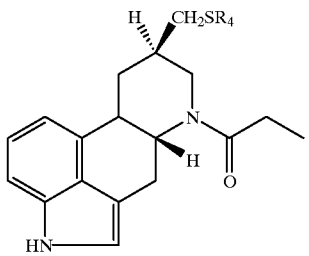

V wherein R$_4$ is, independently, a linear, branched or cyclic, saturated or unsaturated C$_{1-8}$ alkyl residue, such as, for example, the radicals methyl, ethyl, propyl, butyl, isobutyl, tert-butyl, pentyl, cyclopentyl, hexyl, cyclohexyl; the preferred molecule is represented by the compound Va (R$_2$=CH$_3$).

DETAILED DESCRIPTION OF THE INVENTION

In order to obtain quantitative conversion of the 8-methoxycarbonylergoline into the intermediate III, a series of acylating agents, such as 3-halo- and 2-halo-propionyl chlorides, were evaluated. The halogen derivatives tested were chlorine, iodine and bromine derivatives.

As is well known to experts in the field, the presence of an electron-attracting group (such as a chlorine, bromine or iodine atom) in the alpha or beta position to an acid chloride increases the latter's reactivity in acylation reactions.

During the research work which led to the present invention, it was hoped to find, by screening reducing agents, a reagent which exhibited a high degree of chemose-lectivity towards the intermediate chlorine derivative of formula II (R$_2$=alogen, R$_2$=H or R$_2$=H, R$_2$=halogen). The reducing agent was intended to replace the halogen in the alpha (or beta) position to the acylamide function with a hydrogen atom and reduce the methoxycarbonyl function in the 8 position to an alcoholic function without reducing the amide group in position 6.

We ascertained experimentally that by using an equimolar amount of 3-chloropropionyl chloride in the presence of a proton acceptor in acetone solution under stirring at room temperature, D-8-methoxycarbonylergoline gave, in addition to the desired product (D-6-(3'-chloropropionyl)-8-methoxycarbonylergoline; compound IIa), a side product which was subsequently identified as D-6-(acryloyl)-8-methoxycarbonylergoline (compound IIb). The presence of this side product IIb was initially regarded as a critical factor for the industrial development of the process because, even if the presence of compound IIb could be contained by suitably varying the experimental conditions (slow addition of the acylating agent, low reaction temperatures, low concentrations of the reagents) nothing was known of the possible influence of that secondary product on the subsequent synthetic steps.

Surprisingly, the screening carried out on a number of reducing agents under various experimental conditions on a mixture constituted to the extent of 50% by compound IIb and compound IIa demonstrated not only that calcium borobydride in tetrahydrofuran was capable of showing the desired chemoselectivity (removal of the chlorine in position 3' and reduction of the 8-methoxycarbonyl group without reducing the amide in position 6) but also that compound IIb was converted into the desired compound of formula III.

The surprising reactivity of the double bond of compound rib with calcium borohydride in tetrahydrofuran gave us the possibility, which was not foreseeable from the literature, of using the reaction mixture obtained directly from the acylation reaction of D-8-methoxycarbonylergoline without purification in the subsequent reaction step.

Thus, by reacting a mixture of D-8-methoxycarbonylergoline in an aprotic solvent, in concentrations ranging from 8 to 18% weight/volume, under stirring at room temperature, with an equimolar amount of a suitable proton acceptor and one equivalent of 3-halo- or 2-halo-propionyl chloride for a period ranging from 30 minutes to 2 hours, we obtained, after dilution with water and filtration, a mixture of which approximately 50% was constituted by compound IIa and compound IIb.

Aprotic solvents that may be used in that step are represented by acetone, methyl ethyl ketone, tetrahydrofuran, dimethylformamide, preferably acetone; proton acceptors that may be used are triethylamine, pyridine and lutidine, preferably triethylamine.

The mixture of compound IIa and compound IIb is dispersed in tetrahydrofuran with sodium borohydride (from 5 to 9 moles per mole of substrate) and the suspension so obtained is added, at a temperature ranging from 0 to +15° C. and under vigorous stirring, to a tetrahydrofaran solution or to an alcoholic solution (methanol, ethanol or isopropanol) or an aqueous-alcoholic solution containing calcium chloride (from 1.5 to 2 moles per mole of sodium borohydride). When the addition is complete, the temperature is increased to 60° C. and the reaction mixture is maintained under stirring for a period ranging from 20 minutes to 60 minutes. The compound III so obtained is precipitated from the reaction mixture (after acidification of the reaction mixture, evaporation of the organic phase and treatment with aqueous carbonate) and recovered by filtration.

Alternatively, the calcium borohydride, instead of being produced "in situ", can be used already preformed in the commercially available forms (for example, as a bis-THF complex).

On the basis of the data obtained, compound III can be prepared in accordance with Scheme 1 with total yields of 81% starting from D-8-methoxycarbonylergoline.

It was clear from the results obtained that, in order to synthesise the compound of formula III, it would have been equally advantageous to acylate compound I directly with acryloyl chloride (Scheme 3) or to use the intermediate IIa with a high degree of chemical purity (obtainable by the acylation of compound I with chloropropionyl chloride carried out at low temperatures (0–5° C.) and high dilutions (0.05–0.2 molar); Scheme 2) and to reduce the intermediate IIb or IIa so obtained with calcium borohydride in the next step. An experimental check carried out on those two variants confirmed total yields of compound III from compound I superimposable on those obtained by synthesis Scheme 1, confirming the validity thereof as alternatives for obtaining compound III.

Compound III was subsequently reacted, in solution with a proton acceptor, with an alkylsulphonyl chloride under stirring at room temperature for a period ranging from 1 to 2 hours to give compound IV (X=R$_5$SO$_3$; wherein R$_5$ is methyl, ethyl or p-tolyl) with yields ranging from 88 to 95%.

Suitable proton acceptors are represented by pyridine, triethylamine, lutidine, preferably pyridine. Alkylsulphonyl chlorides that may be used are represented by, but not limited to, methanesulphonyl chloride, ethanesulphonyl chloride or p-toluenesulphonyl chloride, preferably methanesulphonyl chloride.

Compound IVa is then treated with from 4 to 8 equivalents of sodium alkyl mercaptide (compound of the general formula $R_4SNa$; wherein $R_4$ is. independently, a linear, branched or cyclic, saturated or unsaturated $C_{1-8}$ alkyl residue) in dimethylformamide with agitation at from 90 to 100° C. for a period ranging from 2 to 5 hours to give compound V with yields ranging from 90 to 95% and an HPLC titre of 97%.

If the $R_4$ group of the allyl mercaptide is an alkyl radical larger than methyl or ethyl, compound IVa ($X=R_5SO_3$; wherein $R_5$ is methyl, ethyl or p-tolyl) can be converted beforehand into a halogenated derivative IVb (preferably X=I) in order to facilitate nucleophilic substitution. That last step is carried out in acetone solution with agitation at reflux temperature in the presence of lithium iodide to give compound IVb in quantitative yields.

Compound V is converted into the final compound VI by treating a heterogeneous mixture of compound V in an aprotic solvent with a reducing agent at a temperature ranging from 20 to 45° C. for from 2 to 6 hours. Reducing agents that may be used in that step are lithium aluminium hydride or sodium dihydrido-bis(2-methoxyethoxy) aluminate; the preferred reducing agent is sodium 7dihydridro-bis(2-methoxyethoxy)aluminate. Aprotic solvents that may be used in that step are tetrahydrofuran, dioxane and toluene; the preferred solvent is toluene. The yields of that step are from 80 to 99%.

The physico-chemical characteristics of the product VI obtained ($R_4=CH_3$) are in good agreement with the data reported in literature for this product; the HPLC purity is 96%.

The high degree of purity of the pergolide base obtained (HPLC titre of 96% on the crude reaction material), the high global yields of the process (66%) starting from D-8-methoxycarbonylergoline and the ready availability of the primary starting material make this process competitive compared with those known from the prior art.

Several salts of compound VI (Pergolide) may be prepared, including acid addiction salts of inorganic acids as well as salts derived from non toxic organic salts. The preparation of the above salts, and particularly the methanesulfonate (mesylate), may be easily realised following known literature procedures, as for example U.S. Pat. No. 4,166,182 and EP-0003667, herein incorporated as references.

EXAMPLES

Example 1

Preparation of D-6-n-propionyl-8-hydroxymethylergoline (Compound III) According to Reaction Scheme 1

A mixture of D-8-methoxycarbonylergoline (compound 1) (10.8 g; 0.04 mol) is heated with vigorous agitation in acetone (100 ml) at 40° C. for 30 minutes, and then at 55° C. for a further 30 minutes. After cooling to ambient temperature, triethylamine (0.04 mol) is added. After a few minutes, a solution of 3-chloropropionyl chloride (5.08 g; 3.84 ml; 0.04 mol) in acetone (5 ml) is added dropwise while maintaining the reaction temperature at from 20 to 25° C. When the addition is complete, the reaction mixture is maintained under stirring at room temperature for 30 minutes, then it is poured into water (150 ml) and the suspension so obtained is maintained under stirring for 30 minutes. After that time, the precipitated solid is recovered by filtration, washed with water (100 ml) and dried overnight under vacuum at a temperature of 60° C. to give 12.8 g of a 6/4 mixture of compound IIa and compound IIb.

For analysis purposes, the two compounds IIa and IIb can be isolated by chromatography on silica gel while eluting with dichloromethane/methanol=9/1.

D-6-(3'-chloropropionyl)-8-methoxycarbonylergoline (Compound IIa):

TLC=$R_f$: 0.72 (eluant dichloromethane/methanol=9/1); $^1$H-NMR (60 MHz, DMSO-$d_6$) gives the diagnostic signals (ppm): 0.50–1.50 (m); 2.10–2.90 (m); 3.30 (s); 2.90–4.00 (m); 6.30–6.75 (m, 4H, aromatic); Elemental analysis: calculated for $C_{19}H_{21}N_2O_3Cl$; theoretical—C: 63.24%; H:5.87%; N:7.76%; O:13.30%; Cl:9.83%; found—C:63.29%; H:5.84%; N:7.67%; Cl:9.88%.

D-6-(acryloyl)-8-methoxycarbonylergoline (Compound IIb)

TLC=$R_f$:0.61 (eluant dichloromethane/methanol=9/1) MS(EI)-$M^+$: m/e=324; $^1$H-NMR (60 MHz, DMSO-$d_6$) gives the diagnostic signals (ppm): 2.15–2.40 (m, 3H); 2.40–3.20 (m, 3H); 3.25 (s, 3H, $CO_2CH_3$); 3.60–3.70 (m, 3H); 5.35–5.70 (m, 2H, $CH_2$=CH); 6.15 (m, 1H, $CH_2$=CH); 6.30–7.15 (m, 4H, aromatic); 9.25–9.50 (sb, 1H, N—H); Elemental analysis calculated for $C_{19}H_{20}N_2O_3$; theoretical—C:70.35%; H:6.21%; N:8.64%; O:14.80%; found—C:70.31%; H:6.26%; N:8.73%.

The mixture of compounds IIa and IIb (1 g), which are obtained directly from the previous reaction, is dispersed in tetrahydrofuran (4 ml) with sodium borohydride (870 mg). The suspension so obtained is added, under vigorous stirring at a temperature of 10° C., to a solution constituted by calcium chloride (14.5 mmol) in ethanol (16 ml). When the addition is complete, the temperature of the reaction mixture is slowly increased to 60° C. and the mixture is maintained under stirring at that temperature for 30 minutes. After that time, the reaction mixture is concentrated under vacuum and the residue so obtained is acidified with 2N HCl; the suspension so obtained is maintained under stirring for 1.5 hours at ambient temperature and then the precipitate is recovered by filtration. The solid so obtained is resuspended in methanol (8 ml); the heterogeneous mixture is heated to reflux temperature and is maintained at that temperature for 10 minutes. When the suspension has been cooled to 15° C., a 10% (15 ml) potassium carbonate solution is added with vigorous stirring. The crystalline solid so obtained is recovered by filtration, washed with a large amount of water and dried under vacuum at a temperature of 60° C. to give 965 mg of compound III (81% total yield from compound I).

TLC=$R_f$: 0.55 (eluant dichloromethane/methanol=9/1) Melting point: 214–216° C.; MS(EI)-$M^+$: m/e=298; $^1$H-NMR (60 MHz, DMSO-$d_6$) gives the diagnostic signals (ppm): 0.85–1.25 (t, 3H, $CH_3CH_2C$=O); 2.15–2.80 (m); 2.85–4.00(m); 4.55–4.85 (sb, 1H, O—H); 6.35–7.05 (m, 4H, aromatic); 10.25–10.50 (sb, 1H, N—H).

Example 2

Preparation of D-6-(propionyl)-8-mesyloxymethylergoline (Compound IVa)

Methanesulphonyl chloride (0.962 g) is added slowly to a solution of compound III (0.984 g) and pyridine (5.900 g) under vigorous stirring and while maintaining the reaction temperature comprise between 15 and 20° C. When the addition is complete, the reaction mixture is maintained under stirring at room temperature for 1 hour, then it is worked up by adding a 10% aqueous solution of potassium carbonate (15 ml) and continuing agitation until a crystalline solid is obtained which is recovered by filtration, washed with a large amount of water and dried under vacuum at 60° C. to give 1.091 g of compound IV (88% yields). HPLC (Column: LICHROCART 125×4 mm packed with LICHROSPHER RP-18, 5 m; mobile phase: 60% buffer 20 mM of $K_2HPO_4$ adjusted to pH 6.5 using $H_3PO_4$ (85%) and 10 mM triethylamine; 40% acetonitrile; flow 1.2 ml/minute): rt 4'266". Elemental analysis calculated for $C_{19}H_{24}N_2O_4S$ theoretical—C:60.62%; H:6.43%; N:7.44%; O:17.00%; S:8.52%; found—C:60.66%; H:6.49%; N:7.45%; S:8.48%.

Example 3

Preparation of D-6-(propionyl)-8-methylthiomethylergoline (Compound V)

Compound IV (1.091 g) is suspended in anhydrous dimethylformanide (6.825 g) and the reaction mixture so obtained is heated (60–80° C.) under stirring until a homogeneous solution is obtained. After cooling to ambient temperature, a 20% solution of sodium methyl mercaptide (5.250 g) in methanol is added rapidly under vigorous stirring. After 1 hour, the reaction mixture is slowly heated until a temperature of 90–95° C. is reached, distilling off all of the methanol. The reaction mixture then continues to be heated under vigorous stirring for 4 hours. The reaction mixture is cooled to 10° C. and 7.5 ml of water are added under stirring. The precipitated product is recovered by filtration, washed with water and dried under vacuum at a temperature of 60° C. to give 0.905 g of compound V (95% yield).

TLC=$R_f$0.81 (eluant dichloromethane/methanol=9/1); HPLC (same experimental conditions as in Example 2)=rt:11'070"; Melting point:268° C. (decomposition); Elemental analysis calculated for $C_{19}H_{24}N_2OS$; theoretical—C:69.48%; H:7.36%; N:8.53%; O:4.87%; S:9.76%; found—C:69.51%; H:7.31%; N:8.48%; S:9.78%.

Example 4

Preparation of D-6-n-propyl-8-methylthiomethylergoline (Compound VI)

4.0 g of a 70% solution of sodium dihydrido-bis(2-methoxyethoxy)aluminate in toluene are added slowly to a suspension of compound V (0.905 g) in toluene (13.8 ml) under stirring at room temperature. When the addition is complete, the reaction is maintained under stirring for 1 hour then heating to a final temperature of 45° C.; this temperature is maintained for 4 hours. At the end of that time, the reaction mixture is cooled to ambient temperature and acidified with 5% HCl (25 ml). The two-phase mixture is distilled under vacuum until the organic phase has been eliminated; the aqueous suspension which remains is filtered under vacuum and the solid so recovered is washed with water. The crude material so obtained is resuspended in methanol (6 ml) and the suspension so obtained is heated under reflux for 30 minutes, then cooled to room temperature and treated with a 10% aqueous solution of potassium carbonate (12 ml) under vigorous stirring. After 2 hours under stirring at room temperature, the suspension is filtered and the solid so recovered is washed with water and dried under vacuum at a temperature of 60° C. to give 0.826 g of compound VI (95% yield).

The physico-chemical characteristics of the product obtained are in good agreement with the literature data (as reported in U.S. Pat. No. 4,166,182). The HPLC titre (same experimental conditions as those given in Example 2) of compound VI so obtained (rt 11'070") is 96%.

Example 5

Preparation of D-6-(propionyl)-8-hydroxymethylergoline (Compound III) According to Reaction Scheme 3

5 g (18.49 mmol) of D-8-methoxycarbonylergoline (Compound I) are dispersed in acetone (50 ml) and the reaction mixture is heated at 40° C. for 30 minutes and then at 55° C. for a further 30 minutes. After cooling to ambient temperature, triethylamine (2.24 g; 3.1 ml; 22.18 mmol) and a solution of acryloyl chloride (2 g; 1.8 ml; 22.18 mmol) in acetone (5 ml) are added in succession while maintaining the reaction temperature comprise between 20 and 25° C. When the addition is complete, the reaction mixture is maintained under stirring at room temperature for 1 hour. The reaction mixture is worked up by being poured into water (100 ml) and maintaining the resulting suspension under stirring for 30 minutes. After that time, the precipitated solid is recovered by filtration, washed with water (80 ml) and dried under vacuum at a temperature of 60° C. to give (5.4 g; 16.64 mmol; 90% yield) of compound IIb.

The physico-chemical characteristics of the resulting product IIb are the same as those of the product obtained by chromatographic purification in Example 1. Compound IIb is then reduced using calcium borohydride produced "in situ", as already described in Example 1, to give compound III with total yields of 78% starting from compound I.

Example 6

Preparation of D-6-(propionyl)-8-hydroxymethylergoline (Compound III) According to Reaction Scheme 2

A mixture of D-8-methoxycarbonylergoline (Compound I) (3.48 g; 12.9 mmol) is heated, under vigorous stirring in acetone (65 ml) at 40° C. for 30 minutes and then at 55° C. for a further 30 minutes. When the reaction mixture has been cooled to 5° C., triethylamine (13 mmol) is added and, while maintaining that temperature, a solution of 3-chloropropionyl chloride (1.64 g; 1.24 ml; 12.9 mol) in acetone (6.5 ml) is added within a period of 30 minutes under vigorous stirring. When the addition is complete, the reaction mixture is maintained under stirring at room temperature for 30 minutes and then it is poured into water (100 ml), the resulting suspension being maintained under stirring for 30 minutes. After that time, the precipitated solid is recovered by filtration, washed with water (35 ml) and dried overnight under vacuum at a temperature of 60° C. to give 3.6 g of compound IIa (contaminated to the extent of 5% with compound IIb). The crude product can be reduced using calcium borohydride produced "its situ" as described in Example 1 to give compound III with total yields, starting from intermediate I, of 80%.

Example 7

Preparation of D-6(propionyl)-8-iodomethylergoline (IVb) Starting From Compound IVa A mixture constituted by compound IVa (1 mmol; 376 mg) and lithium iodide (4 mmol; 455 mg) in acetone (20 ml) is stirred at reflux for 8 hours. After that time, the reaction mixture is worked up by diluting it with water (20 ml) and recovering the resulting solid by filtration, washing it with a large amount of water on the filter and drying it overnight under vacuum at 60° C. 392 mg (0.96 mmol) of compound IVb are recovered.

MS(EI)-$M^+$: m/e=408; Elemental analysis calculated for $C_{18}H_{21}N_2OI$; theoretical—C:52.95%; H:5.18%; N:6.86%; O:3.92%; I:31.08%; found—C:52.90%; H:5.12%; N:6.81%; I:31.12%.

What is claimed is:

1. A process for the preparation of a compound of formula VI,

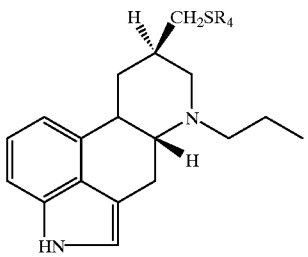

wherein $R_4$ is a saturated or unsaturated $C_{1-8}$ alkyl radical, comprising the following steps:

a) reacting a compound of formula I

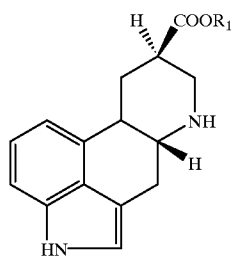

wherein $R_1$ represents a saturated or unsaturated $C_{1-8}$ alkyl residue, with 3-halo-propionyl chloride or 2-halo-propionyl chloride in an aprotic organic solvent in the presence of a proton acceptor;

b) reacting the compound or mixture of compounds obtained in step a) with calcium borohydride in tetrahydrofuran at a temperature of between 10 and 65° C.;

c) reacting the compound obtained in step b) in an aprotic organic solvent with an alkylsulphonyl chloride in the presence of a proton acceptor;

d) reacting the compound obtained in step c) in an aprotic organic solvent with a compound of formula $R_4SX$, wherein $R_4$ has the meaning given above and X is an alkali metal; and e) converting the compound obtained in step d) to compound VI by treatment with a reducing agent in an aprotic organic solvent.

2. A process according to claim 1, wherein the aprotic organic solvent mentioned in point a) is selected from acetone, methyl ethyl ketone, tetrahydrofuran and dimethylformamide.

3. A process according to claim 1, wherein the proton acceptor mentioned in point a) is selected from triethylamine, pyridine and lutidine.

4. A process according to claim 1, wherein both the proton acceptor and the 3-halo- and/or 2-halo-propionyl chloride mentioned in point a) are used in equimolar amounts relative to compound I.

5. A process according to claim 1, wherein reaction a) is carried out at ambient temperature.

6. A process according to claim 1, wherein in reaction b), the calcium borohydride is used in amounts of from 5 to 9 moles/mole of substrate.

7. A process according to claim 1, wherein in reaction b), the tetrahydrofuran is present in amount of from 2 to 8 ml per gram of substrate.

8. A process according to claim 1, wherein in reaction b), the tetrahydrofuran is used in admixture with protic organic solvents or with an aqueous-alcoholic solution thereof.

9. A process according to claim 8, wherein the protic organic solvents are selected from methanol, ethanol and isopropanol.

10. A process according to claim 1, wherein reaction b) is carried out at a temperature of 60° C.

11. A process according to claim 1, wherein reaction c) is carried out at a temperature of between 10 and 30° C.

12. A process according to claim 1, wherein the proton acceptors mentioned in point c) are selected from pyridine, triethylamine, lutidine.

13. A process according to claim 1, wherein the alkylsulphonyl chlorides mentioned in point c) are selected from methanesulphonyl chloride, ethanesulphonyl chloride and p-toluenesulphonyl chloride.

14. A process according to claim 1, wherein the proton acceptor and the alkylsulphonyl chloride mentioned in point c) are preferably used in amounts of from 20 to 30 and 1.2 to 3 moles, respectively, per mole of substrate.

15. A process according to claim 1, wherein $R_4$ is methyl.

16. A process according to claim 1, wherein in reaction d), X is sodium.

17. A process according to claim 1, wherein the compound $R_4SX$ mentioned in point d) is used in an amount of from 4 to 8 equivalents relative to the substrate.

18. A process according to claim 1, wherein the apolar organic solvent mentioned in point d) is dimethylformamide.

19. A process according to claim 1, wherein reaction d) is carried out at a temperature of from 90 to 100° C.

20. A process according to claim 1, wherein reaction e) is carried out at a temperature of from 20 to 45° C.

21. A process according to claim 1, wherein the reducing agents mentioned in point e) are selected from lithium aluminum hydride and sodium dihydridro-bis(2-methoxyethoxy) aluminate.

22. A process according to claim 1, wherein the aprotic solvents mentioned in point e) are selected from tetrahydrofuran, dioxane and toluene.

23. A process according to claim 1, wherein before carrying out reaction d), the compound obtained by reaction c) is converted into the corresponding halogenated derivative.

24. A process according to claim 1, wherein said 3-halo-propionyl chloride is 3-chloro-propionyl chloride.

25. A process for the manufacture of pergolide mesylate wherein it comprises a process according to claim 1.

26. A compound having the formula:

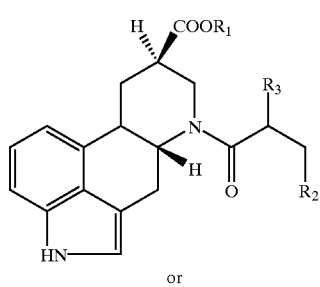

or

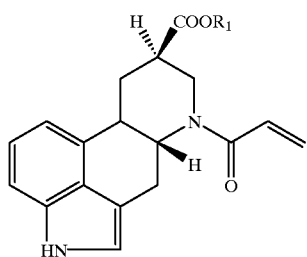

wherein $R_2$ and $R_3$ are halogen and hydrogen, respectively, and $R_1$ represents a saturated or unsaturated $C_{1-8}$ alkyl residue.

27. A compound of formula III

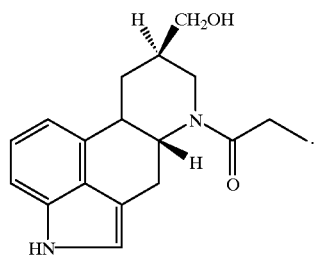

28. A compound of formula IV

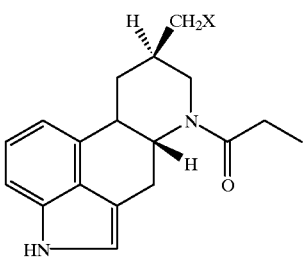

wherein X is a halogen or a compound of the general formula $R_5SO_3$— and $R_5$ is selected from methyl, ethyl, p-tolyl.

29. A compound of formula V wherein $R_4$ is a saturated or unsaturated $C_{1-8}$ alkyl residue.

* * * * *